US005885583A

United States Patent [19]

Miyazaki et al.

[11] Patent Number: 5,885,583

[45] Date of Patent: Mar. 23, 1999

[54] METHOD FOR INHIBITING HYPERLIPEMIA WITH EMMEISOU OR AN EXTRACT THEREOF

[75] Inventors: Toshitsugu Miyazaki; Kunio Kosaka, both of Kobe; Miyako Kakuma, Chuo-ku, all of Japan

[73] Assignee: Nagase & Company, Ltd., Osaka, Japan

[21] Appl. No.: 986,405

[22] Filed: Dec. 8, 1997

[51] Int. Cl.[6] .................................................. A61K 35/786

[52] U.S. Cl. .................................................. 424/195.1

[58] Field of Search .................................................. 424/195.1

[56] References Cited

U.S. PATENT DOCUMENTS 5,676,957 10/1997 Nakamura et al. .................... 424/401

5,716,800 2/1998 Meybeck et al. .................... 435/52

FOREIGN PATENT DOCUMENTS 48-5911 1/1973 Japan .

59-005176 1/1984 Japan .

01172333 7/1989 Japan .

05310537 11/1993 Japan .

09-262066 10/1997 Japan .

*Primary Examiner*—William R. A. Jarvis

*Attorney, Agent, or Firm*—Jacobson, Price, Holman & Stern, PLLC

[57] ABSTRACT

The present invention provides methods for inhibiting hyperlipemia which is responsible for various diseases such as arteriosclerosis, which comprise administering to a subject emmeisou or an emmeisou extract.

3 Claims, No Drawings

METHOD FOR INHIBITING HYPERLIPEMIA WITH EMMEISOU OR AN EXTRACT THEREOF

TECHNICAL FIELD

The present invention relates to a food composition and a pharmaceutical composition for inhibiting (preventing and/or treating) hyperlipemia which is responsible for various diseases such as arteriosclerosis. More particularly, it relates to a food composition and a pharmaceutical composition for inhibiting hyperlipemia which comprises emmeisou or an emmeisou extract as an active ingredient.

BACKGROUND ART

The eating habits of people in developed countries have become richer along with economical development, and fat-intake has gradually increased. However, an excessive fat-intake destroys the balance of the amount of lipids in the blood and causes hyperlipemia. In the present specification, "hyperlipemia" describes conditions in which one or more cholesterols, triglycerides, lipoproteins and/or phospholipids that are lipid components in serum are at an increased level, i.e., it means hypercholesterolemia, hypertriglyceridemia, etc. There is an intimate correlation between hyperlipemia and adult diseases of the circulatory system such as arteriosclerosis. Nowadays, many people suffer from these diseases and it has become a social problem.

At present, drugs such as clofibrate, probucol or nicotinic acid are used as a medicament for treating hyperlipemia, but all of these drugs have side effects. Accordingly, a new medicament is required which exhibits less side effects and is safer to use.

The problem addressed by the present invention was to provide a food composition and a pharmaceutical composition for inhibiting hyperlipemia which is responsible for various diseases such as arteriosclerosis, said compositions being very safe to use and having excellent effects.

DISCLOSURE OF THE INVENTION

In order to solve the above problem, the present inventors have intensively searched for a medicament which is effective in lowering the amounts of total cholesterols, triglycerides, β-lipoproteins and/or phospholipids in blood. As a result, they found that emmeisou and its extract are very effective in lowering the above blood components.

Thus, the present invention provides a food composition and a pharmaceutical composition for inhibiting hyperlipemia which comprise emmeisou or an emmeisou extract as an active ingredient.

Emmeisou has been used as a stomachic with a bitter taste in folk medicine since ancient times. The effects of emmeisou have been disclosed in literature, for example, effects such as an anti-microbial effect [Japanese Patent Publication (Kokai) No. 172333/1989], an anti-neoplastic effect [Japanese Patent Publication (Kokai) No. 5176/1984], an anti-ulcerative effect [Japanese Patent Publication (Kokai) No. 5911/1973], and a hair growth stimulating effect [Japanese Patent Publication (Kokai) No. 310537/1993]. However, it was not known before that emmeisou or its extract has an anti-hyperlipemia effect.

BEST MODE FOR PRACTICING THE INVENTION

The term "emmeisou" used in the present invention refers to a group of plants belonging to the Labiatae family and the Isodon genus and generally called "emmeisou", and includes *Isodon japonisus, Isodon trichocarpus, Isodon sikokianus var. intermodius* or the like. Such an emmeisou can be used as it is or after drying. It is advantageous to use a galenical, "emmeisou" (leaves and stems), which is marketed as a dried product. Such an emmeisou may be cut or ground and the resultant product may be added to a food composition or a pharmaceutical composition without further processing.

Alternatively, an extract of the above emmeisou may be added to a food composition or a pharmaceutical composition according to the present invention. Although the emmeisou extract may be extracted using any means, it is conventional to use an extract obtained using an organic solvent or water or a mixture thereof. The extract may be used as it is, after it has been concentrated or diluted, or after the solvent has been evaporated off. Accordingly, the form of the extract may be the unaltered extracted solution, or a concentrated or diluted solution, or a dried or granulated product.

Examples of the organic solvent used in the extraction are methanol, ethanol, n-propanol, acetone, ethyl acetate, ether, methylene chloride, chloroform, benzene, carbon tetrachloride, petroleum ether and the like, methanol or ethanol being particularly preferred. Although the extraction may be carried out at room temperature, it is desirable to carry out the extraction under the reflux temperature of the solvent used. Although the extraction time varies depending on the extraction temperature, it usually terminates after 2 to 48 hours. After the extraction, filtration or centrifugation is carried out to obtain a crude extract and post-treatment such as concentration, dilution or drying is carried out, if desired.

Forms such as granules, tablets, jelly, confectionery and drinks can be exemplified as the food compositions according to the present invention containing emmeisou or an emmeisou extract, and one can take these compositions when required.

The materials used for preparing the food compositions may be those usually used in this field and include, for example, lactose, dextrose, sucrose, sorbitol, mannitol, apple fibers, soybean fibers, meat extracts, kurozu (black vinegar) extracts, gelatin, corn starch, honey, animal and vegetable fats, polysaccharides or the like.

Forms such as ointments and plasters (as external agents) and forms such as tablets, pills, powders, syrups, emulsions, solutions, suspensions and gelatin capsules (as internal agents) can be exemplified as the pharmaceutical compositions. In addition, forms such as injections and sprays may be exemplified. These compositions may be administered, for example, via a transdermal, oral, injection or intranasal route.

Examples of carriers used for preparing the pharmaceutical compositions are lactose, dextrose, sucrose, sorbitol, mannitol, starch, acacia gum, calcium phosphate, alginates, calcium silicate, microcrystalline cellulose, polyvinylpyrrolidone, cellulose derivatives, tragacanth, gelatin, syrups, methyl hydroxybenzoate, talc, magnesium stearate, water, mineral oils and the like.

The present food and pharmaceutical compositions may also contain lubricants, emulsifying or suspending agents, antioxidants, preservatives, sweetening and/or flavoring agents, and may further contain other active ingredients (including water-soluble vitamins, oil-soluble vitamins and the like). The present food and pharmaceutical compositions comprising these ingredients may be produced according to a conventional method well known in the art.

The emmeisou extract used for the present food and pharmaceutical compositions is effective over a wide dose range. Accordingly, the dose per day of the emmeisou extract may generally be in the range from about 0.01 mg to 1,000 mg, preferably in the range from about 0.1 mg to 500 mg, and more preferably in the range from 1 mg to 200 mg, per kg body weight. Such a dose may be taken or administered all at one time or in fractions over several times. However, the actual dose is determined after considering the age, body weight and severity of the condition of the subjects to be treated as well as the administration route selected.

EXAMPLES

The present invention is further illustrated by the following examples, but it is not limited thereto.

Example 1

Preparation of emmeisou extract

To 320 kg of emmeisou (whole plant, roughly cut), 3,200 kg of water was added and the extraction was carried out at a temperature of more than 95° C. for one hour. After the mixture was cooled to 65° C., it was centrifuged to obtain an extract. Then, 2,560 kg of water was again added to the residue and the extraction was carried out in a similar manner to obtain an extract. The second extract was combined with the first extract and the mixture was concentrated under a reduced pressure at 40° C. to obtain 130 L of a concentrated extract. The extract was spray-dried to obtain 38 kg of an emmeisou extract.

Example 2

Effect of emmeisou extract on hyperlipemia

Evaluation of the effect on hyperlipemia was carried out using a hyperlipemia model induced by Triton WR-1339. The emmeisou extract prepared in Example 1 was orally administered to a group of S1c Wister rats (male, 7 weeks old) in a dose of 200 mg/kg, once a day, continuously for 7 days. Before the administration, as well as at 6, 12, 24, 48 and 72 hours after the administration, blood samples were taken from the aorta abdominalis of the ether-anesthetized rats. Sera were separated from the blood samples, and the amounts of cholesterol, triglyceride and phospholipid were measured by an enzymatic method and the amounts of β-lipoprotein were measured by nephelometry.

As a control, rats receiving 200 mg/kg of probucol were evaluated in a similar manner. The results of the evaluation are shown in Tables 1 to 4. It is apparent from the results that the concentrations in serum of cholesterol, triglyceride, β-lipoprotein and phospholipid components which are substances responsible for hyperlipemia were reduced by the administration of the emmeisou extract.

TABLE 1

Effect of emmeisou extract on cholesterol inhibition

| | | Cholesterol concentration in serum (mg/100 ml) | | | | | |
|---|---|---|---|---|---|---|---|
| | | before | | | after | | |
| Sample | Dose | administration | 6 hrs | 12 hrs | 24 hrs | 48 hrs | 72 hrs |
| Control | 0 | 48 ± 0.3 | 103 ± 6.7 | 82 ± 4.8 | 59 ± 2.8 | 64 ± 2.6 | 64 ± 0.3 |
| Emmeisou extract | 200 mg/kg × 7 | 50 ± 2.0 | 86 ± 1.5 | 55 ± 4.3* | 57 ± 1.8 | 74 ± 5.0 | 70 ± 4.9 |
| Probucol | 200 mg/kg × 2 | 49 ± 2.2 | 93 ± 6.5 | 61 ± 4.6* | 58 ± 2.6 | 69 ± 1.9 | 65 ± 0.9 |

*P < 0.05: Significant to control group by 5%(*) of significance level in Turkey muitiple comparison test

TABLE 2

Effect of emmeisou extract on triglyceride inhibition

| | | Triglyceride concentration in serum (mg/100 ml) | | | | | |
|---|---|---|---|---|---|---|---|
| | | before | | | after | | |
| Sample | Dose | administration | 6 hrs | 12 hrs | 24 hrs | 48 hrs | 72 hrs |
| Control | 0 | 71 ± 5.3 | 794 ± 66.8 | 350 ± 55.9 | 225 ± 14.5 | 93 ± 9.2 | 119 ± 10.4 |
| Emmeisou extract | 200 mg/kg × 7 | 68 ± 6.8 | 507 ± 24.3* | 122 ± 22.9** | 170 ± 23.2 | 100 ± 10.3 | 86 ± 7.4 |
| Probucol | 200 mg/kg × 2 | 60 ± 10.8 | 608 ± 62.1 | 166 ± 26.1* | 194 ± 8.8 | 109 ± 5.3 | 135 ± 11.8 |

*P < 0.05, **P < 0.01: Significant to control group by 5%(*), 1%(**) of significance level in Turkey multiple comparison test

TABLE 3

| Effect of emmeisou extract on β-lipoprotein inhibition | | | | | | | |
|---|---|---|---|---|---|---|---|
| | | β-Lipoprotein concentration in serum (mg/100 ml) | | | | | |
| Sample | Dose | before administration | 6 hrs | 12 hrs | after 24 hrs | 48 hrs | 72 hrs |
| Control | 0 | 82 ± 5.3 | 389 ± 44.8 | 508 ± 75.1 | 400 ± 18.5 | 169 ± 13.6 | 180 ± 14.7 |
| Emmeisou extract | 200 mg/kg × 7 | 66 ± 3.9 | 275 ± 28.2 | 210 ± 36.7* | 287 ± 30.8* | 183 ± 14.3 | 146 ± 8.5 |
| Probucol | 200 mg/kg × 2 | 66 ± 12.7 | 332 ± 56.2 | 277 ± 44.6* | 339 ± 18.0 | 190 ± 8.5 | 201 ± 18.9 |

*P < 0.05: Significant to control group by 5%(*) of significance levels in Turkey mutliple comparison test

TABLE 4

| Effect of emmeisou extract on phospholipid inhibition | | | | | | | |
|---|---|---|---|---|---|---|---|
| | | Phospholipid concentration in serum (mg/100 ml) | | | | | |
| Sample | Dose | before administration | 6 hrs | 12 hrs | after 24 hrs | 48 hrs | 72 hrs |
| Control | 0 | 94 ± 0.8 | 201 ± 12.0 | 127 ± 7.7 | 126 ± 3.4 | 133 ± 4.0 | 139 ± 2.3 |
| Emmeisou extract | 200 mg/kg × 7 | 98 ± 3.5 | 162 ± 3.0* | 90 ± 4.7* | 121 ± 0.7 | 144 ± 6.7 | 146 ± 7.3 |
| Probucol | 200 mg/kg × 2 | 95 ± 1.4 | 176 ± 7.4 | 99 ± 6.3* | 123 ± 4.2 | 146 ± 3.1 | 146 ± 1.1 |

*P < 0.05: Significant to control group by 5%(*) of significance level in Turkey multiple comparison test Example 3

Emmeisou extract toxicity test

The emmeisou extract (2,000 and 4,000 mg/kg/day) was orally administered to a group of Crj:CH(SD) male rats (5 weeks old; 11 rats/group), repeatedly for 28 days. As a result, it was found that no abnormality was seen in general conditions, body weights, changes in the amounts of feeds taken, urine observations, hematological observations, hematochemical observations, organ weight observations, anatomicopathological observations and histopathological observations of the rats. Thus, an amount of more than 4,000 mg/kg/day of the emmeisou extract was non-toxic for the male rats.

Example 4

Food A

A foodstuff having the following composition was prepared using the emmeisou extract obtained in Example 1.

TABLE 5

| Ingredient | Weight (kg) |
|---|---|
| Emmeisou extract | 0.04 |
| Soybean saponin | 2.0 |
| Kurozu extract | 2.0 |
| Apple fiber | 2.0 |
| Lecithin | 1.0 |
| Fructooligosaccharide | 2.0 |
| Fructose | 1.0 |
| Powdered vinegar | 0.1 |
| Cyclodextrin | 1.0 |
| Honey | 1.0 |
| Bone powder | 1.0 |
| Dextrin | 4.9 |

All the ingredients were mixed in a flow granulator, water was sprayed to granulate the mixture, and the granules formed were dried at an introduced air temperature of 80° C.

Example 5

Food B

A foodstuff having the following composition was prepared using the emmeisou extract obtained in Example 1.

TABLE 6

| Ingredient | Weight (kg) |
|---|---|
| Emmeisou extract | 0.01 |
| Soybean saponin | 0.5 |
| Kurozu extract | 0.5 |
| Apple fiber | 0.5 |
| Soybean fiber | 0.5 |
| Fructose | 1.0 |
| Cyclodextrin | 3.0 |
| Gelatin | 3.5 |

The above ingredients were thoroughly mixed with 10 kg of water and the mixture was then heated to 60° C. to obtain a paste.

The paste was added to 50 kg of soybean oil previously heated to 70° C. and the mixture was thoroughly mixed in an agitator equipped with two anchor-type agitating blades. After confirming that the paste was dispersed in the soybean oil, the mixture was cooled to 5° C. and filtered to separate out the particles formed. The particles thus obtained were washed with n-hexane and then dried to obtain microcapsules containing the above ingredients.

Example 6

Hard gelatin capsule

Hard gelatin capsules were prepared using the following ingredients.

TABLE 7

| Ingredient | Amount (mg/capsule) |
|---|---|
| Emmeisou extract | 250 |
| Starch | 100 |
| Cellulose | 100 |
| Magnesium stearate | 10 |
| Total | 460 mg |

Example 7

Tablet

Tablets were prepared using the following ingredients.

TABLE 8

| Ingredient | Amount (mg/tablet) |
|---|---|
| Emmeisou extract | 250 |
| Cellulose | 400 |
| Silicon dioxide | 10 |
| Stearic acid | 5 |
| Total | 665 mg |

Example 8

Suspension

A suspension was prepared using the following ingredients.

TABLE 9

| Ingredient | Amount used |
|---|---|
| Emmeisou extract | 50 mg |
| Sodium carboxymethylcellulose | 50 mg |
| Syrup | 1.25 ml |
| Benzoic acid solution | 0.10 ml |
| Flavoring agent | q.v. |
| Coloring agent | q.v. |
| Pure water | to total 5 ml |

Example 9

Intravenous preparation

An intravenous preparation was prepared using the following ingredients.

TABLE 10

| Ingredient | Amount used |
|---|---|
| Emmeisou extract | 100 mg |
| Isotonic saline | 1000 ml |

As described above, the emmeisou extract was added to food and pharmaceutical compositions as an active ingredient for inhibiting various diseases caused by hyperlipemia. When administering these food and pharmaceutical compositions to animals, good results were obtained.

INDUSTRIAL UTILIZATION

The present food and pharmaceutical compositions containing emmeisou or an emmeisou extract as an active ingredient are very safe to use and are superior in terms of lowering effects on the amounts of total cholesterols, triglycerides, β-lipoproteins and phospholipids in blood. Thus, these compositions are effective for inhibiting various diseases such as arteriosclerosis, which are caused as a result of hyperlipemia.

What is claimed is:

1. A method of treating hyperlipemia in a subject in need thereof which comprises administering to the subject an effective amount of emmeisou or an emmeisou extract.

2. A method of claim 1 which comprises administering emmeisou to the subject.

3. A method of claim 1 which comprises administering an emmeisou extract to the subject.

* * * * *